United States Patent [19]
Butler et al.

[11] Patent Number: 5,951,985
[45] Date of Patent: *Sep. 14, 1999

[54] TUMOR ASSOCIATED EPITOPE

[75] Inventors: Sandra M. Butler, Laurel; Nicholas Pomato, Frederick, both of Md.; Ebo Bos, Oss, Netherlands; Michael G. Hanna, Jr., Frederick; Martin V. Haspel, Seneca, both of Md.; Herbert C. Hoover, Jr., Center Valley, Pa.

[73] Assignee: Perimmune Holdings, Inc., Rockville, Md.

[ * ] Notice: This patent issued on a continued prosecution application filed under 37 CFR 1.53(d), and is subject to the twenty year patent term provisions of 35 U.S.C. 154(a)(2).

[21] Appl. No.: 08/960,128

[22] Filed: Aug. 19, 1997

Related U.S. Application Data

[63] Continuation of application No. 08/478,591, Jun. 7, 1995, abandoned.

[51] Int. Cl.⁶ .......................... A61K 39/00; A61K 38/00; G01N 33/574; C07K 16/00
[52] U.S. Cl. .................... 424/185.1; 435/7.23; 530/326; 530/388.8
[58] Field of Search ........................ 424/185.1; 435/7.23; 530/326, 388.8

[56] References Cited

U.S. PATENT DOCUMENTS

| | | | |
|---|---|---|---|
| 4,810,781 | 3/1989 | Hollinshead | 530/413 |
| 4,828,991 | 5/1989 | Hanna et al. | 435/68 |
| 4,997,762 | 3/1991 | Hanna et al. | 435/240.27 |
| 5,106,738 | 4/1992 | Hanna et al. | 435/172.2 |
| 5,338,832 | 8/1994 | Pomato et al. | 530/350 |
| 5,474,755 | 12/1995 | Hanna et al. | 424/1.49 |

OTHER PUBLICATIONS van Grunsven et al, "Gene mapping and expression of two immunodominant Epstein–Barr virus capsid proteins", J. of Virol., vol. 67, pp. 3908–3916, Jul. 1993.

Bader et al, "Amino acid sequence and gene organization of cytokeratin No. 19, an exceptional tail–less intermediate filament protein", EMBO J., vol. 5, No. 8, pp. 1865–1875, 1986.

Krauss et al, "Organization and sequence of the human gene encoding cytokeratin 8", Gene, vol. 86, pp. 241–249, 1990.

J.E. Strickler et al, *Analytical Biochemistry*, 140:553–566 (1984).

S. Kraus et al., *Gene*, 86 (1990) 241–249.

W.M.J. can Grunsven et al., *Journal of Virology*, 67:3908–3916 (1993).

De Jager, R. et al., "Current Status of Cancer Immunodetection with Radiolabeled Human Monoclonal Antibodies," *Seminars in Nuclear Medicine*, vol. XXIII, No. 2, pp. 165–179, Apr., 1993.

*Primary Examiner*—Sheela Huff
*Assistant Examiner*—Yvonne Eyler
*Attorney, Agent, or Firm*—William M. Blackstone

[57] ABSTRACT

This invention relates to the epitopes to which monoclonal antibody 88BV59 and antibody 16.88 react. These antibodies were produced by B-cell lines derived from B-cells of cancer patients actively immunized with autologous tumor antigens. Both epitopes are found on the same antigen in tumor tissue. These epitopes can be used in both diagnostic procedures and therapy for human cancers.

3 Claims, 4 Drawing Sheets

Cytokeratin 8:   ValLeuGluValAspProAsnIleGlnAlaValArgThrGlnGluLysGluGln

RPHPLC Peak 1:   ValLeuGluValAspProAsnIleGlnAlaValArgThrGlnGluLysPheGln (8 cont'd) IleLysThrLeuAsnAsnLysPheAlaSerPheIleAspLysValArgPheLeuGluGlnGlnAsn (1 cont'd) IleLysThrLeuAsnAsnLysPheAlaSerPheIleAspLysValArgPheLeuXxxGlnGlnAsn

FIG. 3

TUMOR ASSOCIATED EPITOPE

This application is a continuation of U.S. Ser. No. 08/478,591, filed Jun. 7, 1995, now abandoned.

FIELD OF THE INVENTION

This invention relates to epitopes targeted by monoclonal antibodies produced by hybridoma or transformed B-cell lines derived from B-cells of cancer patients actively immunized with autologous tumor antigen. These epitopes can be used in both diagnostic procedures and therapy for human cancers, as well as for screening antibodies and antibody fragments.

BACKGROUND OF THE INVENTION

We have identified the epitopes targeted by human monoclonal antibodies that react specifically with antigens associated with particular cancers. This invention also relates to diagnostic procedures, antibody screening and cancer therapy using these epitopes as targets and as active portions of immunogens.

Antibodies are protein molecules normally synthesized by B-cell lymphocytes produced by bone marrow and carried in the blood stream. For any antigen in the body, i.e., any foreign or non-self self molecule, from a simple organic chemical to a complex protein, antibodies are produced that recognize and attach to that particular chemical structure. The unique chemical structure on the antigen to which a particular antibody can bind is referred to as an antigenic determinant or epitope. B-cell lymphocytes in the body, referred to as B-cells, lymphocytes, or leukocytes, exist as hundreds of millions of different genetically programmed cells, each producing an antibody specific for a different epitope. An antigen, which stimulates antibody production, can have several epitopes on its surface. On encountering an antigen, a B-cell carrying on its surface an antibody specific for an epitope on that antigen will replicate. This clonal expansion results in many daughter cells that secrete that antibody into the blood stream.

Because of the specificity of antibodies in recognizing and binding to antigens, it was desired to identify antibodies that are specific for a single epitope, thus binding only to antigens or tissues having that particular epitope. Once the epitope was identified it was available for screening antibodies produced by cell lines, and even for immunopurifying antibodies from polyclonal serum. As part of a larger molecule, synthetic or natural, the epitope can also be used as an effective immunogen.

Monoclonal antibodies are synthesized in pure form uncontaminated by other immunoglobulins. With monoclonal antibody producing cells it is possible to produce virtually unlimited quantities of an antibody that is specific for one epitope on a particular antigen. Antibodies specific for particular cancer can be used in various methods of treatment and diagnosis.

Monoclonal antibodies increase the specificity of chemotherapeutic drugs, toxins and radioactive isotopes, thus increasing their efficacy while decreasing their toxicity by dramatically reducing the quantities required. In addition, antibodies conjugated with radionuclides or metallic tracers can be used for imaging for in vivo diagnosis and localization of metastases, such as with proton emission (PET), nuclear magnetic resonance (NMR), computed tomography (CT), and planar and single photon emission computed tomography, and for use in labeling tumor tissue to be identified during surgery using a probe. The antibodies can also be used for detecting the presence of tumor antigens in blood, as a diagnostic or prognostic test for cancer.

The existence of antigens associated with animal tumors was documented in the last century, and the antigenic character of human cancers has been well established, primarily through recent studies with monoclonal antibodies. However, until the research that resulted in this invention, few cancer antigens have actually been characterized in molecular terms and only one group of antigenic determinants associated with human cancers, immunoglobulin idiotypes of B-cell tumors, has been described as being uniquely tumor-specific, i.e., occurring with a high frequency on tumor cells and not occurring to any significant degree on normal tissues (Oldham and Smalley, *J. Biol. Response Modifiers*, 1983; Stratte et al, *J. Biol. Response Modifiers*, Volume 1, 1982).

Past attempts at deriving monoclonal antibodies specific for human cancers have taken two routes with respect to B-cells: 1) B-cells have been extracted from spleens of mice that were immunized against human tumors, U.S. Pat. No. 4,172,124; and 2) human B-cells have been extracted from either peripheral blood or from lymph nodes draining tumors in cancer patients. Neither approach has yielded satisfactory results.

Mice immunized against human tumors have too broad a reactivity. That is, most of the mouse monoclonal antibodies generated react with human antigens present on normal as well as on tumor tissue. An antibody that reacts only with tumor cells is very difficult to select from among the large variety of antibodies produced. For example, 20,000 hybridomas derived from mice immunized with human small-cell lung carcinoma were screened for reactivity with tumor cells (*Science*, 1982, 216:283), resulting in a very low frequency (<0.4%) of reactivity observed by this research group. By contrast, the present invention results in up to 16% of the hybridomas derived from immunized colon patients produce monoclonal antibodies that react specifically with tumor cells. In addition, monoclonal antibodies derived from mouse B-cells have limited potential for application in cancer therapy. After repeated administration they stimulate the human immune system to produce "anti-mouse" antibodies which, in clinical trials, have been shown to neutralize the activity of mouse monoclonal antibodies. The use of our human monoclonal antibodies can circumvent these difficulties.

Another apparent difference between human and mouse monoclonal antibodies is their pattern of labeling. Previous studies with mouse antibodies have demonstrated that there is often a heterogenous labeling of cells within tumor sections. This pattern of reactivity has been attributed by some authors to antigenic heterogeneity of tumor cells (Hand et al., *Cancer Research*, 43:728–735, 1983). In contrast, the human monoclonal antibodies developed by our strategy were homogeneous in terms of their reactivity with tumors to which they did react. A plausible explanation for the heterogenous staining of mouse monoclonal antibodies is that it is a reflection of the murine immune recognition of phase- or cell-cycle-specific differentiation antigens abundant on the tumor cells rather than putative tumor associated antigens. It is not unreasonable to expect that when one immunizes mice with human tumor cells there would be substantial antigenic competition resulting in the more abundant and more predominant tissue-type and differentiation antigens successfully competing with proportionally fewer tumor associated antigens for immune responsiveness by the host. Thus, autologous immunization of man may result in the elicitation of antibodies against the group of antigens normally poorly immunogenic in mice. This evidence suggests that humans and mice may respond to different tumor antigens. In concert with this hypothesis is our finding that none of the first 36 human monoclonal antibodies we produced appeared to react with carcinoembryonic antigen (CEA), an antigen frequently recognized by murine monoclonal antibodies made against human tumor cells.

The major problem in creating monoclonal antibodies specific for human tumor antigens has been the inability to find a source of specifically immune B-cells (*Science*, 1982, 216:285). In humans, the initial foci of cancer cells tend to grow over long periods of time, from 1% to 10% of the human lifespan, before there is any palpable clinical evidence of the disease. By this time patients are immunologically hyporesponsive to their tumors, or possibly immunologically tolerant. Thus, prior to this work, the development of human monoclonal antibodies specific for tumor associated antigens and the identification of their target epitopes could not reproducibly be obtained.

Identification of the tumor specific epitopes of the present invention resulted from research beginning with efforts to develop monoclonal antibodies specifically reactive with tumor-associated antigens that induced an immune response in patients having particular cancers. This was a new and more effective approach for obtaining monoclonal antibodies using peripheral blood B-cells from patients immunized with cells from their own tumors in specific vaccine preparations. To achieve active specific immunotherapy, patients were immunized with cells from their own tumors. Humans mounting an objective immune response against tumor cells were specifically found to be a good source of activated B-cells. The peripheral blood of these patients, who had been actively immunized against their own tumors, was an abundant source of such activated B-cells.

Clinical studies demonstrated that an objective immune response is generated on treating patients having the particular cancer by skin testing, i.e., delayed cutaneous hypersensitivity (DCH). Immunized patients showed delayed cutaneous hypersensitivity to their own colorectal cancers. In addition, the monoclonal antibodies developed from the immunized patient's B-cells reacted with tumors of the same histological type in other patients. These results indicated that the patient's humoral immune response, production of antibodies, was directed against colorectal cancer antigens generally and was not unique to the immunized patient's own tumor. This general response, which indicated that there are specific antigens associated with tumors that contain unique epitopes, is especially important for the development of a standardized vaccine.

The generation of B-cells that produce antibodies having reactivity specific for particular epitopes on tumor cell associated antigens, particularly cell surface antigens as in the majority of cases, is an advantageous result that was speculative, at best, when the immunization studies were begun. So, too, was the discovery that these are particular epitopes that are presented by tumor cells, and are found to a comparatively small degree expressed in normal tissue. Only the immunization treatment was observed and measured during the animal studies on which the human immunization procedures were based, not the production of tumor specific antibodies.

The general immune response accompanied by an improvement in the subject's condition was indicative of a cellular response in which macrophages and T-cells become activated in the presence of tumor cell antigens and destroy the tumor cells. Although an antibody response would predictably be triggered by immunization under most circumstances, the time course of the antibody response and the cellular response would in most instances be different. Moreover, the fact that the patients were being immunized with autologous tumor cells, i.e., the patient's own tumor cells, and the experience of previous investigators that little or no antibody production is triggered by a patient's own tumor, made the discovery that B-cells that produce tumor specific antibodies are generated after immunization an unexpected beneficial result. We then discovered that there are tumor specific antigens having epitopes that are uniquely effective targets.

Some cellular and humoral immune responses can occur independently of each other. For example, it is possible to mount a humoral response in the absence of demonstrable cellular immunity. Conversely, potent cellular immunity, particularly delayed cutaneous hypersensitivity (DCH), may develop despite a minimal antibody response. It was surprising, therefore, for the subjects who showed a positive response to active immunotherapy to have been excellent sources of B-cells producing tumor specific antibodies, particularly to cell surface antigens.

The isolation of B-cells that produce tumor specific antibodies required the preparation of successful vaccines for active specific immunization, procedures for extracting immunized B-cells, the production of monoclonal antibody producing cell lines and the production of monoclonal antibodies. Malignant tumors were digested using enzyme preparations. The cells obtained were treated to yield a non-tumorigenic tumor cell preparation having the requisite cell viability, which was injected as a vaccine into the subject from which the tumor was obtained. Peripheral blood B-cells were obtained from the inoculated subject after a predetermined interval and were used to prepare monoclonal antibody producing cells by fusing with myeloma cells, after which the fused cells were screened for the synthesis of immunoglobulin. Monoclonal antibody producing cells were also obtained by selecting spontaneously transformed B-cells that were able to survive in continuous culture, and by exposing B-cells to an agent capable of transforming cells, such as Epstein Barr Virus (EBV) or another lymphotropic virus.

Larger amounts of antibodies were obtained by fusing EBV-transformed cells with mouse myeloma cells and human-mouse heteromyelomas. Cells that synthesized immunoglobulin were tested for production of antibodies that react with antigens characteristic of the malignant tissue. Those selected were cultured to produce monoclonal antibodies that react with the particular type of tumor with which the subject was afflicted. Our identification of novel epitopes reactive with these antibodies makes direct screening for other useful immunoglobulins possible. The monoclonal antibodies identified can be used as radioimmunoscintography (RIS) agents for diagnostic purposes and for carrying therapeutic agents to primary tumor and metastatic sites. The epitopes themselves are also directly useful for isolating antibodies directed against tumor antigens and as targets for in vivo imaging and therapy, and for in vitro tissue analysis. They may also be used, when combined with larger molecules, as immunogens for immunotherapy and for antibody production.

Identification of epitopes after raising monoclonal antibodies is not assured of success because antigen sequence information is normally not available, the antigens may not be simple proteins, and the epitopes themselves may be three dimension conformational epitopes with little or no reactivity in linear sequences. The present epitopes could only be identified and sequenced after our discovery that the 16.88 and 88BV59 antibodies reacted with certain cytokeratins for which sequence information was available.

SUMMARY OF THE INVENTION

This invention is directed to tumor associated epitopes found on the tumor antigen CTAA 16.88. They are the 88BV59 epitope found on CTAA 16.88 and on native cytokeratin 8, and comprising the amino acid sequence TyrSerLeuGlySerSerPheGly SerGlyAlaGlySerSerSerPheSer [SEQ ID NO:1], and the 16.88 epitope found on CTAA 16.88, which is homologous to epitopes found on cytokeratins 8, 18 and 19, and which comprises the amino acid sequence ThrLeuGlnGlyLeuGluIleGluLeuGlnSerGlnLeuSerMetLys [SEQ ID NO:7], and functional fragments and equivalents thereof.

BRIEF DESCRIPTION OF THE FIGURES

FIG. 3 illustrates the homology between a cytokeratin 8 partial sequence and an 88BV59 epitope sequence.

DETAILED DESCRIPTION OF THE EMBODIMENTS

Figure 1:
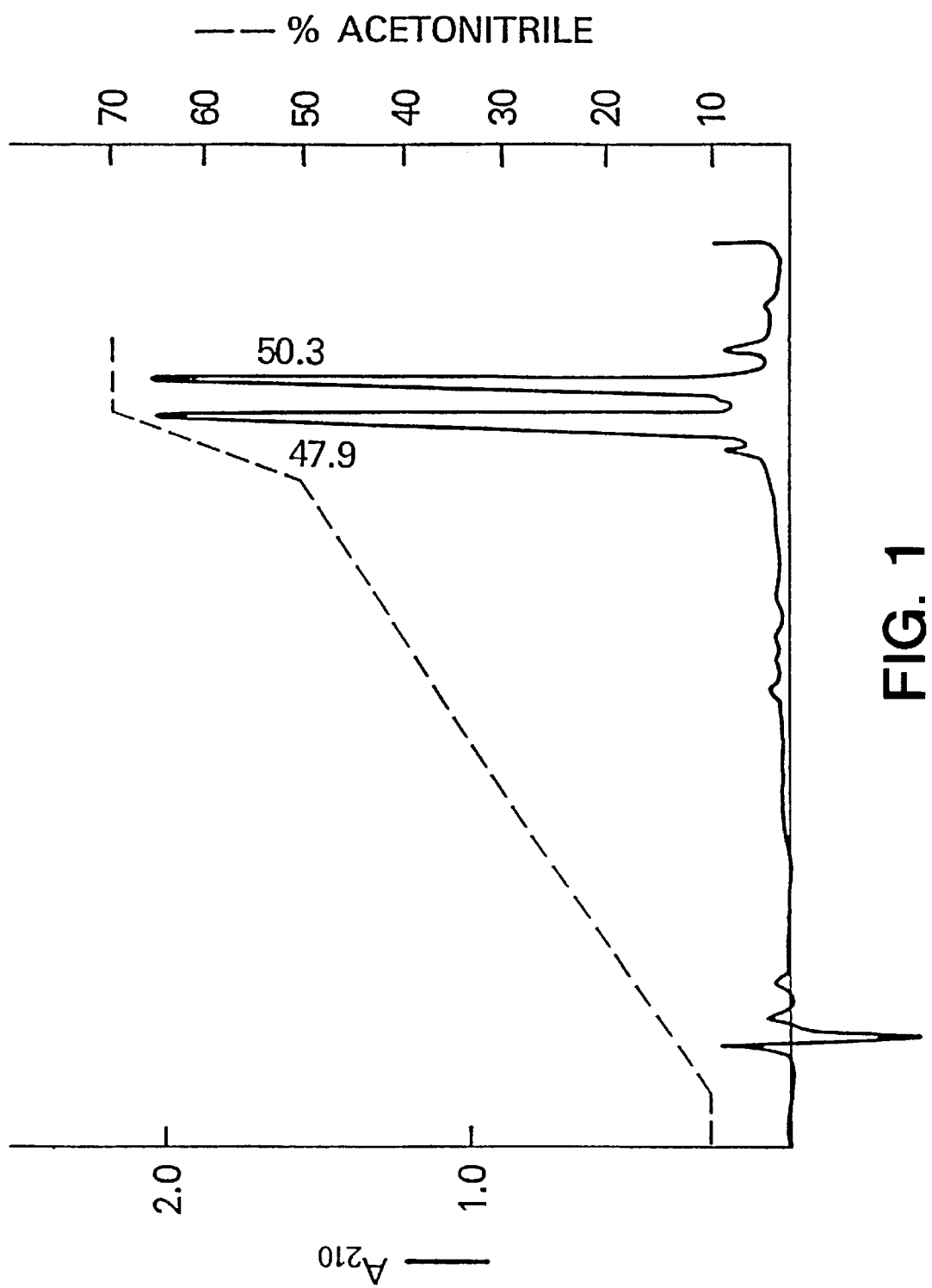
FIG. 1 shows the reverse phase high performance liquid chromatography (RPHPLC) profile of CTAA 16.88.

Monoclonal Antibody 88BV59, described in U.S. application Ser. No. 08/192,089 filed Feb. 4, 1994, included herein by reference, has been shown to recognize an antigen designated as colon tumor associated antigen (CTAA) 16.88, also refered to as CTA #1. This antigen was claimed in U.S. Pat. No. 5,338,832, issued Aug. 16, 1994, also included herein by reference. CTAA 16.88 was first identified using human IgM antibody 16.88 (MCA 16.88), defined in U.S. Pat. No. 4,997,762 issued Mar. 5, 1991, included herein by reference. Both the MCA 88BV59 and MCA 16.88 recognize the same tumor associated antigen, but react with different epitopes on that antigen. Monoclonal Antibody 88BV59 was deposited under the terms of the Budapest Treaty on Dec. 13, 1990, with the American Type Tissue Culture Collection, 10801 University Boulevard, Manassas, Va. 20110-2209, under the ATCC accession No. CRL 10624. In addition, the cell lines 88BV59H21-2 and 88BV59H21-2V67-66 were deposited on Jan. 31, 1994, with the American Type Tissue Culture Collection, 10801 University Boulvard, Manassas, Va. 20110-2209, under the ATCC accession Nos. CRL 11538 and CRL 11539.

Targeting the epitopes of the invention (88BV59 epitope and 16.88 epitope) provides a means for diagnosis and therapy of cancer. MCA 88BV59 and MCA 16.88 labeled by conventional methods with radioisotopes or metallic tracers have been used in radiological scanning. Isotopes that may be used include, but are not limited to, iodine-131, iodine-125, indium-111 and technetium-99m. The specific activity of the radiolabeled antibody is not particularly limited, and about 2 to about 4 mCi/mg. of antibody have been found to be acceptable. For example, about 15 to about 41 mCi of $^{99m}$TC-88BV59 have been infused intravenously over a 30 minute period and good imaging resulted. This amount may be varied depending on such factors as weight of the patient and the type of isotope. Other methods of introduction of the radiolabeled antibody into the body may be used, such as through intralymphatic and intraperitoneal administration. Similarly, MCA 16.88 has also proven itself useful for tumor imaging. $^{111}$In-LiLo-16.88 administered by an intramammary route was used for the presurgical staging of primary breast cancer. Also, planar imaging of colorectal cancer with $^{131}$I-16.88 was positive in at least 75% of the patients in two studies. The details of immunodetection with radiolabeled MCA 88BV59 and MCA 16.88 are found in the review article, DeJager et al., "Current Status of Cancer Immunodetection with Radiolabeled Human Monoclonal Antibodies", *Seminars in Nuclear Medicine*, Volume XXIII, No. 2 (Apr.), 1993: pages 165–179, the contents of which are incorporated herein by reference. The administration of both radiolabeled MCA 88BV59 and radiolabeled MCA 16.88 has been shown to be safe and well tolerated with few side effects reported.

The data collected so far clearly indicate that antibody scanning with $^{99m}$TC-88BV59 using both planar and tomographic techniques is superior to CT scanning for the detection of intraabdominal and pelvic metastases. The combination of the two modalities appears to give optimal detection. In addition, probes that detect radiation have been used during surgery to identify tumor and metastatic tissue for resection. Any antibody with specificity for the 88BV59 epitope or the 16.88 epitope will be useful for identifying tumor tissue. Human monoclonal antibodies like MCA 88BV59, MCA 16.88 and fragments thereof provide the advantage of not being immunogenic.

A further important use of the 88BV59 or 16.88 epitopes is screening of antibodies raised against tumor tissue to identify antibodies that would be useful in the clinic for imaging tumors and for targeting tumors with therapeutic agents. Antibodies can also be identified by such screening to be used in the clinical laboratory for identifying or confirming the presence of tumor tissue.

88BV59 showed negative reactivity with the following normal human tissues: ovary, uterus, testes, vagina, adrenal glands, prostate, thyroid, thymus, lymph nodes, spleen, bone marrow, myocardium, cerebral cortical cells, skin, muscle and hemopoietic cells. 88BV59 exhibited slight reactivity with the following tissues: colon (brush border and superficial glands), small intestine (brush border and superficial glands), stomach (gastric pits and superficial glands), esophagus (glands), pancreas (some ductal and exocrine glandular epithelium), kidney (50% of collecting tubules), cervix (epithelial lining (⅔ tissues were positive)), breast (acini and ductal epithelium), lung (some alveolar and bronchial cells), brain (astrocytes (⅔ tissues were positive)), spinal cord (neuropil), skin (50% of glands in dermis) and liver (bile ducts). Reactivity of 88BV59 with human tumor cell lines is shown in Table 2. Table 3 shows the reactivity of 88BV59 with tumor tissue specimens. The results of these studies indicated that, even though normal tissue would be expected to contain native cytokeratin 8, which contains the 88BV59 epitope, the epitope has practical utility for identifying tumor tissue. The reactivity of MCA 16.88 with normal and tumor tissues is already described in U.S. Pat. No. 4,997,762 (e.g., in Example II), and in U.S. Pat. No. 5,338,832, both of which are already included herein by reference. Both epitopes appear to be more strongly expressed in tumor cells, or the epitope may be masked in normal tissue. In either case, both 88BV59 and 16.88 epitopes are useful for targeting and identifying tumor tissue.

CTAA 16.88 is a complex of polypeptides (under denaturing conditions) in a molecular weight range of 35–43 KD. Within this complex of polypeptides, there are epitopes related to intermediate filament proteins, specifically cytokeratins 8, 18 and 19. Monoclonal antibodies specific for these cytokeratins have been shown to cross-react with this tumor associated antigen. MCA 88BV59 binds to a subset of the polypeptides recognized as CTAA 16.88 (within the molecular weight range described). It has been shown that the native antigen, which behaves as a single protein entity under non-denaturing conditions, such as size exclusion chromatography and native polyacrylamide gel electrophoresis, is separable into two components by reverse phase high performance liquid chromatography. This chromatographic profile is shown in FIG. 1.

Figure 2:
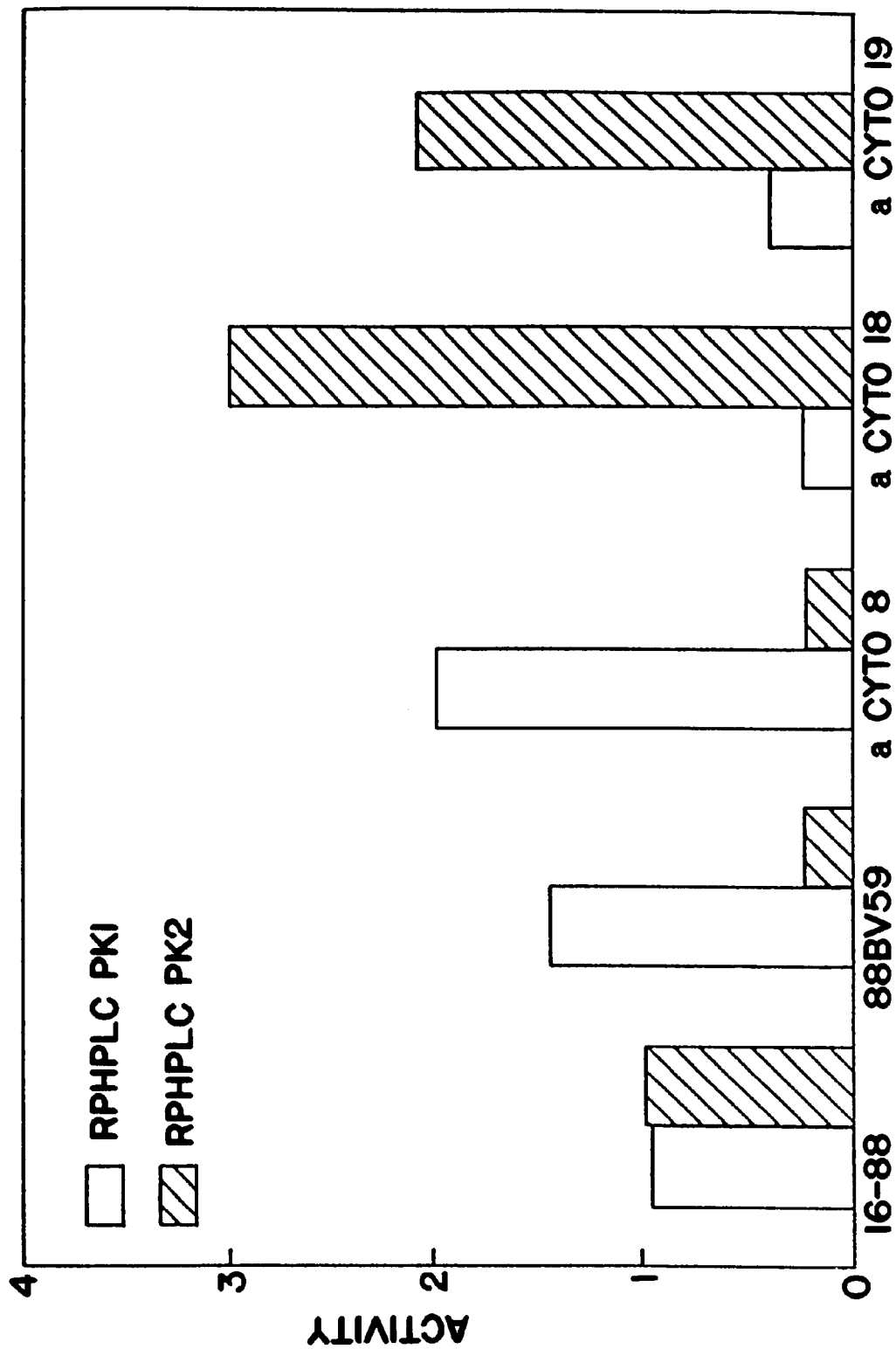
FIG. 2 illustrates the reactivity of MCA 16.88, MCA 88BV59, anti cyto 8 antibody, anti cyto 18 antibody and anti cyto 19 antibody with peak 1 and peak 2 of CTAA 16.88 (CTA #1) by RPHPLC.

An indirect enzyme-linked immunoassay (EIA) demonstrated that MCA 88BV59 predominantly recognizes the first peak obtained in the reverse phase chromatographic profile. This data is depicted in FIG. 2.

In order to further characterize the nature of the immunoreactivity of MCA 88BV59 with CTAA 16.88, we performed N-terminal protein sequence analysis [1]. As can be seen in FIG. 3, the predominant sequence obtained from the polypeptides located within the reverse phase HPLC peak 1 has strong homology with the intermediate filament protein cytokeratin 8. Because it has not been possible to obtain a recombinant form of CTAA 16.88, and because MCA 88BV59 reacts with native cytokeratin 8, we used the protein sequence previously established for cytokeratin 8 in order to determine the epitope specificity of MCA 88BV59.

Figure 4A:
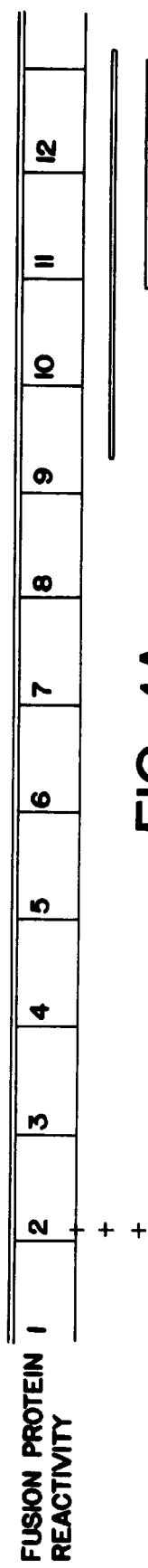
FIG. 4 shows the epitope specificity of MCA 88BV59 by pepscan and by reactivity with portions of cytokeratin 8.

One approach for defining the epitope recognized by an antibody is to synthesize segments of the reactive protein using a bacterial expression system and to then react these peptides with the antibody of interest. Using this strategy, we determined that the carboxyl terminal end of cytokeratin 8 contains the epitope recognized by 88BV59, which is illustrated in FIG. 4A.

Figure 4B:
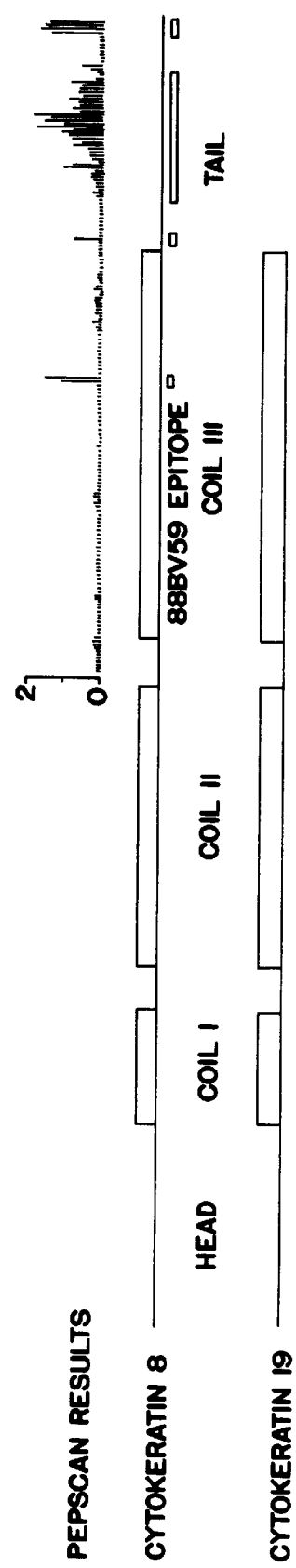

Another approach for defining the epitope recognized by an antibody is the PEPSCAN method, which involves synthesizing short peptides of a defined length beginning at each position along the length of a protein of interest and then reacting the peptides with the antibody of interest. Using this method, we determined that the antibody 88BV59 reacts with a broad portion of the cytokeratin 8 tail region, from amino acids 417–464, with the highest reactivity in the region of amino acids 437–453. Three small regions also showed significant reactivity with the antibody, amino acids 353–366, amino acids 400–411 and amino acids 469–483. This type of reactive profile is typical of conformational epitopes. These results are shown in FIG. 4B.

The epitope targeted by monoclonal antibody 16.88 is an epitope related to cytokeratins 8, 18 and 19, to which 16.88 has been demonstrated to show binding activity. Specifically, the epitope is a polypeptide comprising the amino acid sequence Thr LeuGlnGlyLeuGluIleGluLeuGlnSerGlnLeuSerMetLys (SEQ ID NO:7) or a functional fragment equivalent thereof.

By the term "fragment" we refer to any sequence of amino acids that comprises part of the polypeptide defined by the amino acid sequences for the 88BV59 or 16.88 epitopes, having common structural elements and antibody binding specificity. They are within the scope of the present invention because they can be prepared by persons skilled in the art, given the teachings of the present invention.

As used herein, "functional equivalent" means variations of the recited sequences that still maintain the antibody binding characteristics of the recited amino acid sequences for the 88BV59 and 16.88 epitopes. These functional characteristics are the ability to react with the antibody 16.88.

Variations that can occur in the sequences and still remain functional equivalents include differences in one or more amino acids resulting from deletions, substitutions, insertions, inversions or additions. Amino acid substitutions that are expected to not essentially alter biological and immunological properties have been described. Amino acid replacements between related amino acids or replacements that occur frequently in evolution are, inter alia, Ser/Ala, Ser/Gly, Asp/Gly, Asp/Asn, Ile/Val (see Dayhof, M.D., Atlas of Protein Sequence and Structure, Nat. Biomed. Res. Found., Washington D.C., 1978, vol. 5, suppl. 3). Based on this information Lipman and Pearson developed a method for rapid and sensitive protein comparison (Science 227, 1435–1441, 1985) and for determining the functional similarity between homologous polypeptides. Functional equivalents also include multimeres of the recited amino acid sequence, which provide a multiplicity of binding sites or sites for conjugation. When claiming the invention by reciting the amino acid sequences of the epitopes, the claims are intended to include functional fragments and functional equivalents thereof as defined herein.

EXAMPLE 1

CTAA 16.88 is purified from crude lysates of HT-29 colon tumor cells by ammonium sulfate precipitation, gel filtration chromatography, and affinity or ion exchange chromatography, as described in U.S. Pat. No. 5,338,832. The purified antigen is chromatographed using a Vydac $C_4$ reverse phase chromatography column, which is analyzed on a Waters high performance liquid chromatography system. The column is equilibrated in water containing 0.1% trifluoroacetic acid (TFA). The sample is loaded onto the equilibrated column, washed with the same buffer, and then eluted using a linear gradient starting with water containing 0.1% TFA and progressing to 70% acetonitrile in water containing 0.1% TFA over a 30 minute period, at a flow rate of 1 ml/minute. As illustrated in FIG. 1, under these conditions, two protein peaks are obtained for the purified antigen.

EXAMPLE 2

In order to determine the immunoreactivity of 88BV59 (as well as other antibodies being tested) an enzyme immunoassay was set up. In this assay, microtiter plates were coated with either antigen obtained from peak 1 from the reverse phase column or peak 2 from the column. The concentration of antigen used for coating was 10 $\mu$g/ml in phosphate buffered saline. The plates were coated at 37° C. for 2 hours. After washing with a solution of PBS containing 0.05% Tween, the plates were incubated with various antibodies including MCA 88BV59 at a concentration of 5 $\mu$g/ml. The antibody was allowed to incubate on the plates at room temperature for 2 hours. The plates were then washed with the PBS-Tween solution and then treated with an HRP-labeled goat anti-human Ig(G,A,M) conjugate obtained from KPL Laboratories, Rockville, Md. at a dilution of 1:10,000. The conjugate was incubated on the plates for 1 hour at room temperature and the plates were then washed with the PBS-Tween solution. Color was then developed using the TMB substrate system obtained from KPL Laboratories. As can be seen in FIG. 2, the results of this enzyme immunoassay indicated that 88BV59 reacted strongly with peak 1 from the reverse phase HPLC and much more weakly with peak 2. In addition, by this assay, peak 1 reacted strongly with a monoclonal antibody specific for cytokeratin 8.

EXAMPLE 3

In order to characterize the portion of the CTAA 16.88 antigen recognized by MCA 88BV59, the antigen representing peak 1 from the reverse phase HPLC analysis was used for protein sequence analysis. For this purpose, a gas phase protein sequencer, model 470A, obtained from Applied BioSystems, Inc., Foster City, Calif., was used. Briefly, 500 pm of the antigen was placed on a polybrene-coated filter and inserted into the unit. Amino acids were derivitized with PTH and cleaved sequentially. The cleaved PTH derivitized amino acids were analyzed using an online, microbore HPLC unit (Model 120A). The results of this protein sequence analysis can be seen in FIG. 3, which shows that the sequence obtained from peak 1 of CTAA 16.88 that was reactive with MCA 88BV59 had high homology with the cytokeratin 8 intermediate filament protein.

EXAMPLE 4

DNA corresponding to the coding region of the cytokeratin 8 gene was amplified from HT29 cDNA using oligonucleotide primers designed based on published sequence [2]. This DNA was used as the template in a polymerase chain reaction (PCR) to amplify 3 fragments of the gene, corresponding to amino acids 83–483 (coils I, II, III and tail), 329–483 (C-terminal half of coil III and tail) and 400–483 (tail) as shown in FIG. 4A. These fragments were cloned into the *E. coli* expression/fusion vector pMLB1113, using the EcoRI and BamHI restriction sites, in such a manner that the cytokeratin sequences were expressed fused to amino terminus of β-galactosidase. The samples were tested for the level of expression by analyzing Coomassie stained SDS polyacrylamide gels. Normalized amounts of the fusion proteins were tested for reactivity to the 88BV59 antibody by Western Blot analysis. Briefly, samples of cell lysates of clones producing the fusion proteins were electrophoresed on an 8% polyacrylamide gel and transferred to nitrocellulose. The Western blot was reacted with 88BV59 (5 µg/ml) and then detected using a goat anti-human IgG antibody conjugated to horseradish peroxidase. All three of the fusion proteins reacted with the antibody, therefore it was determined that the C-terminal portion of the molecule contained the epitope. These data are summarized in FIG. 4A.

EXAMPLE 5

To further define the epitope that reacts with 88BV59, the so-called PEPSCAN method [3] was employed. Briefly, the sequence corresponding to the third coil and tail region of the cytokeratin 8 molecule was used to generate 12-mer peptides beginning at each position along the protein segment. Each one of these peptides was allowed to react with 88BV59 in a liquid/liquid type of hybridization. Positive reactivity was assayed by an indirect enzyme linked assay. By this method, it was determined that 88BV59 reacts with a broad region of the cytokeratin tail region, amino acids 417–464, typical of a conformational epitope. The highest reactivity is in the region of amino acids 437–453. Additionally, three small regions also showed significant reactivity with the antibody, amino acids 353–366, amino acids 400–411, and amino acids 469–483. These data are shown in FIG. 4B.

Area of highest reactivity was found in amino acids 437–453: Tyr Ser Leu Gly Ser Ser Phe Gly Ser Gly Ala Gly Ser Ser Ser Phe Ser [SEQ ID NO:1].

Other regions reactive with MCA 88BV59, which alone are individual binding sites and together help form the conformational epitope, include amino acids 353–366

Leu Ser Glu Leu Glu Ala Ala Leu Gln Arg Ala Lys Gln Asp [SEQ ID NO:2], amino acids 400–411:

Ser Arg Leu Glu Ser Gly Met Gln Asn Met Ser Ile [SEQ ID NO:3], amino acids 417–436:

Gly Gly Tyr Ala Gly Gly Leu Ser Ser, Ala Try Gly Asp Leu Thr Asp Pro Gly Leu Ser [SEQ ID NO:4], amino acids 454–464:

Arg Thr Ser Ser Ser Arg Ala Val Val Val Ile [SEQ ID NO:5] and amino acids 469–483:

Arg Asp Gly Lys Leu Val Ser Glu Ser Ser Asp Val Leu Pro Lys [SEQ ID NO:6].

TABLE 1

CRITERIA FOR SUCCESSFUL VACCINES FOR ACTIVE SPECIFIC IMMUNOTHERAPY

Adjuvant (a) BCG (Phipps, Tice, Connaught); Lyophilized, frozen (dose-dependence > $10^6$ ($10^7$–$10^8$))
  (b) *C. parvum* (Wellcome Labs) (dose-dependence > 7 µg (70 µg–700 µg)

Tumor Cells (a) Enzymatic dissociation
    (1) Collagenase type I (1.5–2.0 U/ml HBSS)
    (2) DNAase (450 D.U./ml HBSS)
    (3) 37° C. with stirring
  (b) Cryopreservation
    (1) Controlled-rate freezing (−1° C./min) (7.5% DMSO, 5% HSA, HBSS)
    (2) Viability 80%
  (c) X-irradiation
    (1) Rendered non-tumorigenic at 12,000–20,000 R.

Components and Administration[1]

(a) Ratio of adjuvant to tumor cells - 10:1–1:1 (optimum)
  (b) $10^7$ tumor cells (optimum)
  (c) 2–3 i.d. vaccinations at weekly intervals. Third vaccination contains tumor cells only.

[1]Isoniazid chemoprophylaxis of BCG infection optional.
BCG — Bacillus Calmette Guerin
HBSS — Hanks' Balanced saline solution
DMSO — Dimethylsulfoxide
HSA — Human serum albumin
R — Rads
PBS — Phosphate buffered saline
EDTA — Ethylenediaminetetraacetic acid

TABLE 2

REACTIVITY OF HUMAN MONOCLONAL ANTIBODY 88BV59
Indirect Immunofluorescence with Acetone-filed Tumor Cells[a]

| Cell Line | Tumor Type | Fluorescence Intensity[a] |
|---|---|---|
| Ht-29 | Colon Carcinoma | 3+ |
| SKCO-1[c] | Colon Carcinoma | 3+ |
| LS174 | Colon Carcinoma | 4+ |
| WiDr | Colon Carcinoma | N.T.[e] |
| HCT-8 | Colon Carcinoma | — |
| Bt-20[b] | Breast Carcinoma | 3+ |
| EP[b] | Breast Carcinoma | 2+ |
| MCF-7 | Breast Carcinoma | 4+ |
| SKBR-III | Breast Carcinoma | — |
| CaLu-1[c] | Lung Adenocarcinoma | 4+ |
| A2780 | Ovarian Carcinoma | — |
| Ovcar3[c] | Ovarian Carcinoma | 4+(30%)[d] |
| WI-38 | Normal Fibroblasts | — |

[a]Florescence Intensity: 4+strong, 3+moderate, 2+weak to moderate, 1+weak, —negative. Concentration of 88BV59-1 was 10 µg/ml. Staining with a control human IgG at 10 ηg/ml was negative on all cells.
[b]Staining preferentially on cells in mitosis.
[c]Staining shows a filamentous cytoskeletal staining pattern.
[d]Percentage of cells showing the indicated fluorescence intensity was 100% unless otherwise noted.
[e]NT = not tested.

TABLE 3

REACTIVITY OF 88BV59 WITH VARIOUS TUMOR TYPES

| Tumor Type | Number of Reactive Tissues | Total Number of Tissue Tested | Percentage |
|---|---|---|---|
| Colon | 17 | 23 | 74 |
| Breast | 19 | 19 | 100 |
| Ovarian | 13 | 17 | 76 |
| Pancreatic | 3 | 9 | 33 |
| Lung | 3 | 4 | 75 |
| Prostate | 4 | 6 | 67 |

REFERENCES

1. Strickler, J. E., Hunkapiller, N. W., and Wilson, K. J. Utility of the gas phase sequencer for both liquid and solid phase degradation of proteins and peptides and low picomole levels. Anal. Biochem. 140:553–566, 1984.
2. S. Krauss and W. Franke, Gene 86, 241–249, 1990.
3. van Grunsuen, W. M. J. J. Virol. 67:3908–3916, 1993.

---

We claim:

1. A peptide comprising the amino acid sequence of SEQ ID NO: 1, which is detectable on human tumor cells but is essentially non-detectable on normal cells with monoclonal antibody 88BV59.

2. A peptide comprising at least one amino acid sequence selected from the group consisting of SEQ ID NO: 2, SEQ ID NO: 3, SEQ ID NO: 4, SEQ ID NO: 5, and SEQ ID NO: 6, which is detectable on human tumor cells but is essentially non-detectable on normal cells with monoclonal antibody 88BV59.

3. The peptide of claim 1, comprising, in addition to the amino acid sequence of SEQ ID NO: 1, at least one amino acid sequence selected from the group consisting of SEQ ID NO: 2, SEQ ID NO: 3, SEQ ID NO: 4, SEQ ID NO: 5, and SEQ ID NO: 6.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 17 amino acids
      (B) TYPE: amino acid
      (C) STRANDEDNESS: Not Relevant
      (D) TOPOLOGY: Not Relevant (ii) MOLECULE TYPE: peptide (iii) HYPOTHETICAL: NO (xi) SEQUENCE DESCRIPTION: SEQ ID NO:1:

```
Tyr Ser Leu Gly Ser Ser Phe Gly Ser Gly Ala Gly Ser Ser Ser Phe
1               5                   10                  15
Ser
```

(2) INFORMATION FOR SEQ ID NO:2:

(i) SEQUENCE CHARACTERISTICS:
      (A) LENGTH: 14 amino acids
      (B) TYPE: amino acid
      (C) STRANDEDNESS: Not Relevant
      (D) TOPOLOGY: Not Relevant (ii) MOLECULE TYPE: peptide (iii) HYPOTHETICAL: NO (xi) SEQUENCE DESCRIPTION: SEQ ID NO:2:

```
Leu Ser Glu Leu Glu Ala Ala Leu Gln Arg Ala Lys Gln Asp
1               5                   10
```

(2) INFORMATION FOR SEQ ID NO:3:

(i) SEQUENCE CHARACTERISTICS:
      (A) LENGTH: 12 amino acids
      (B) TYPE: amino acid
      (C) STRANDEDNESS: Not Relevant
      (D) TOPOLOGY: Not Relevant (ii) MOLECULE TYPE: peptide (iii) HYPOTHETICAL: NO (xi) SEQUENCE DESCRIPTION: SEQ ID NO:3:

Ser Arg Leu Glu Ser Gly Met Gln Asn Met Ser Ile
1               5                   10

(2) INFORMATION FOR SEQ ID NO:4:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (xi) SEQUENCE DESCRIPTION: SEQ ID NO:4:

Gly Gly Tyr Ala Gly Gly Leu Ser Ser Ala Tyr Gly Asp Leu Thr Asp
1               5                   10                  15

Pro Gly Leu Ser
            20

(2) INFORMATION FOR SEQ ID NO:5:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (xi) SEQUENCE DESCRIPTION: SEQ ID NO:5:

Arg Thr Ser Ser Ser Arg Ala Val Val Val Ile
1               5                   10

(2) INFORMATION FOR SEQ ID NO:6:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (xi) SEQUENCE DESCRIPTION: SEQ ID NO:6:

Arg Asp Gly Lys Leu Val Ser Glu Ser Ser Asp Val Leu Pro Lys
1               5                   10                  15

(2) INFORMATION FOR SEQ ID NO:7:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (xi) SEQUENCE DESCRIPTION: SEQ ID NO:7:

Thr Leu Gln Gly Leu Glu Ile Glu Leu Gln Ser Gln Leu Ser Met Lys
1               5                   10                  15